US009676800B2

(12) United States Patent
Tenn, III et al.

(10) Patent No.: US 9,676,800 B2
(45) Date of Patent: *Jun. 13, 2017

(54) EXTRACTION SOLVENT CONTROL FOR REDUCING STABLE EMULSIONS

(71) Applicant: INVISTA NORTH AMERICA S.A R.L., Wilmington, DE (US)

(72) Inventors: William J. Tenn, III, Beaumont, TX (US); Sudhir N. V. K. Aki, Katy, TX (US); Thomas E. Vos, Beaumont, TX (US); Tseng H. Chao, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/962,095

(22) Filed: Dec. 8, 2015

(65) Prior Publication Data

US 2016/0083406 A1    Mar. 24, 2016

Related U.S. Application Data

(63) Continuation-in-part of application No. PCT/US2014/043125, filed on Jun. 19, 2014, and a continuation-in-part of application No. PCT/US2014/043132, filed on Jun. 19, 2014, and a continuation-in-part of application No. PCT/US2014/043134, filed on Jun. 19, 2014, and a continuation-in-part of application No. PCT/US2014/043142, filed on Jun. 19, 2014, and a continuation-in-part of application No. PCT/US2014/043394, filed on Jun. 20, 2014.

(60) Provisional application No. 61/837,450, filed on Jun. 20, 2013, provisional application No. 61/837,458, filed on Jun. 20, 2013, provisional application No. 61/837,468, filed on Jun. 20, 2013, provisional application No. 61/837,477, filed on Jun. 20, 2013.

(51) Int. Cl.

| | |
|---|---|
| *B01J 38/56* | (2006.01) |
| *C07F 9/48* | (2006.01) |
| *B01J 31/40* | (2006.01) |
| *B01J 31/18* | (2006.01) |
| *B01D 11/04* | (2006.01) |
| *B01D 11/00* | (2006.01) |

(52) U.S. Cl.
CPC ........ *C07F 9/4841* (2013.01); *B01D 11/0426* (2013.01); *B01D 11/0434* (2013.01); *B01D 11/0488* (2013.01); *B01D 11/0492* (2013.01); *B01J 31/4053* (2013.01); *B01J 38/56* (2013.01); *B01D 2011/002* (2013.01); *B01J 31/1865* (2013.01); *B01J 2231/343* (2013.01); *B01J 2531/847* (2013.01); *Y02P 20/582* (2015.11); *Y02P 20/584* (2015.11)

(58) Field of Classification Search
CPC ............ B01D 11/0426; B01D 11/0434; B01D 2011/002; B01J 2531/847; B01J 31/1865; B01J 31/4053; C07F 9/4841
See application file for complete search history.

(56) References Cited

U.S. PATENT DOCUMENTS

| | | |
|---|---|---|
| 3,496,215 A | 2/1970 | Drinkard et al. |
| 3,496,217 A | 2/1970 | Drinkard et al. |
| 3,496,218 A | 2/1970 | Drinkard |
| 3,773,809 A | 11/1973 | Walter |
| 4,082,811 A | 4/1978 | Shook, Jr. |
| 4,290,880 A | 9/1981 | Leonard |
| 4,339,395 A | 7/1982 | Barnette et al. |
| 4,551,314 A | 11/1985 | Beckstead et al. |
| 5,543,536 A | 8/1996 | Tam |
| 6,924,345 B2 | 8/2005 | Gagne et al. |
| 6,936,171 B2 | 8/2005 | Jackson et al. |
| 7,935,229 B2 | 5/2011 | Deckert et al. |
| 9,011,691 B2 | 4/2015 | Tenn, III et al. |
| 9,133,223 B2 | 9/2015 | Tenn, III |
| 9,133,226 B2 | 9/2015 | Tenn, III |
| 2008/0083607 A1* | 4/2008 | Deckert ............. B01D 11/0434 203/43 |
| 2008/0281119 A1* | 11/2008 | Scheidel ................ C07C 253/34 558/308 |
| 2013/0211126 A1 | 8/2013 | Moerbe et al. |
| 2014/0350280 A1 | 11/2014 | Tenn, III |

FOREIGN PATENT DOCUMENTS

| | | |
|---|---|---|
| DE | 10-2004-045036 A1 | 3/2006 |
| GB | 835282 A | 5/1960 |

(Continued)

OTHER PUBLICATIONS

International Preliminary Report on Patentability received for PCT Patent Application No. PCT/US2014/043125, mailed on Dec. 30, 2015, 10 pages.

(Continued)

*Primary Examiner* — Valerie Rodriguez-Garcia
(74) *Attorney, Agent, or Firm* — Robert B. Furr, Jr.; Edward F. Kenehan, Jr.

(57) ABSTRACT

Disclosed herein are methods for recovering diphosphonite-containing compounds from mixtures comprising organic mononitriles and organic dinitriles, using multistage countercurrent liquid-liquid extraction. Recovery is enhanced with one or more method steps. In a first step, a portion of the heavy phase from the settling section of the first stage is recycled to the settling section of the first stage. In a second step, a portion of the light phase from the settling section of the first stage is recycled to the mixing section of the first stage. In a third step, the first stage takes place in a mixer-settler, a Lewis base is introduced into the settling section of the first stage, and a complex of Lewis acid and Lewis base is formed in this settling section. In a fourth step, a polyamine is added to the first stage.

11 Claims, 4 Drawing Sheets

(56) References Cited

FOREIGN PATENT DOCUMENTS

| WO | 01/36429 A1 | 5/2001 |
| WO | 2013/095853 A1 | 6/2013 |
| WO | 2014/205183 A1 | 12/2014 |
| WO | 2014/205188 A1 | 12/2014 |
| WO | 2014/205190 A1 | 12/2014 |
| WO | 2014/205195 A1 | 12/2014 |
| WO | 2014/205337 A1 | 12/2014 |

OTHER PUBLICATIONS

International Search Report and Written Opinion received for PCT Patent Application No. PCT/US2014/043125, mailer on Sep. 12, 2014, 12 pages.
International Preliminary Report on Patentability received for PCT Patent Application No. PCT/US2014/043132, mailed on Dec. 30, 2015, 8 pages.
International Search Report and Written Opinion received for PCT Patent Application No. PCT/US2014/043132, mailed on Sep. 12, 2014, 10 pages.
International Preliminary Report on Patentability received for PCT Patent Application No. PCT/US2014/043134, mailed on Dec. 30, 2015, 8 pages.
International Search Report and Written Opinion received for PCT Patent Application No. PCT/US2014/043134, mailed on Sep. 12, 2014, 10 pages.
International Preliminary Report on Patentability received for PCT Patent Application No. PCT/US2014/043142, mailed on Dec. 30, 2015, 6 pages.
International Search Report and Written Opinion received for PCT Patent Application No. PCT/US2014/043142, mailed on Sep. 10, 2014, 8 pages.
International Preliminary Report on Patentability received for PCT Patent Application No. PCT/US2014/043394, mailed on Dec. 30, 2015, 6 pages.
International Search Report and Written Opinion received for PCT Patent Application No. PCT/US2014/043394, mailed on Sep. 10, 2014, 8 pages.

* cited by examiner

EXTRACTION SOLVENT CONTROL FOR REDUCING STABLE EMULSIONS

CROSS-REFERENCE TO RELATED APPLICATIONS

This application combines the disclosures of five previously filed, related applications. This application claims benefit of each of the following, related U.S. Provisional Applications: No. 61/837,450, filed Jun. 20, 2013; No. 61/837,458, filed on Jun. 20, 2013; No. 61/837,468, filed Jun. 20, 2013; and U.S. Provisional Application No. 61/837,477, filed on Jun. 20, 2013. The disclosures of these provisional applications are incorporated herein by reference.

This application claims Continuation-in-Part status to each of the following, related International Patent Applications: PCT/US2014/043125 (published as WO 2014/205183 A1), filed Jun. 19, 2014; PCT/US2014/043132 (published as WO 2014/205188 A1), filed Jun. 19, 2014; PCT/US2014/043134 (published as WO 2014/205190 A1), filed Jun. 19, 2014; PCT/US2014/043142 (published as WO 2014/205195 A1), filed Jun. 19, 2014; and PCT/US2014/043394 (published as WO 2014/205337 A1), filed Jun. 20, 2014. The disclosures of these international applications and published counterparts are incorporated herein by reference.

PCT/US2014/043125 (now WO 2014/205183 A1) claims priority to U.S. Provisional Application No. 61/837,450. PCT/US2014/043132 (now WO 2014/205188 A1) claims priority to U.S. Provisional Application No. 61/837,458. PCT/US2014/043134 (now WO 2014/205190 A1) claims priority to U.S. Provisional Application No. 61/837,468. PCT/US2014/043142 (now WO 2014/205195 A1) claims priority to U.S. Provisional Application No. 61/837,477. PCT/US2014/043394 (now WO 2014/205337 A1) claims priority to U.S. Provisional Application No. 61/837,477.

FIELD OF THE INVENTION

The invention relates to recovery of catalyst and ligand from a hydrocyanation reaction product mixture comprising organic dinitriles using liquid-liquid extraction.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phosphite, phosphinite and phosphonite ligands can be used to form nickel-based catalysts to perform such hydrocyanation reactions.

U.S. Pat. No. 3,773,809 describes a process for the recovery of Ni complexes of organic phosphites and phosphonites from a product fluid containing organic nitriles produced by hydrocyanating an ethylenically unsaturated organic mononitrile such as 3-pentenenitrile through extraction of the product fluid with a paraffin or cycloparaffin hydrocarbon solvent. Similarly, U.S. Pat. No. 6,936,171 to Jackson and McKinney discloses a process for recovering diphosphite-containing compounds and phosphinite-containing compounds from streams containing dinitriles.

U.S. Pat. No. 4,339,395 describes the formation of an interfacial rag layer during extended periods of continuous extraction of certain phosphite ligands. The '395 patent notes that the interfacial rag hinders, if not halts, the phase separation. Because the process is operated continuously, the rag must be removed continuously from the interface as it accumulates to avoid interrupting operation. To solve this problem for the disclosed components, the '395 patent discloses the addition of minor amounts of substantially water-free ammonia.

U.S. Pat. No. 7,935,229 describes a process for extractively removing heterogeneously dissolved catalyst from a reaction effluent of a hydrocyanation of unsaturated mononitriles to dinitriles with a hydrocarbon. The catalyst comprises a ligand which may be a monophosphite, a diphosphite, a monophosphonite or a diphosphonite. Ammonia or an amine may be added to a mixture of liquid phases before phase separation takes place.

U.S. Pat. No. 9,011,691, U.S. Published Application No. 2014-0350280 A1, U.S. Pat. No. 9,133,226 and U.S. Pat. No. 9,133,223, each describe a process corresponding to those described in the present disclosure, except that a diphosphite ligand is recovered in the processes of these patents and published application, whereas a diphosphonite ligand is recovered in the process of the present application.

SUMMARY OF THE INVENTION

This process recovers diphosphonite-containing compounds from a mixture comprising diphosphonite-containing compounds, organic mononitriles, organic dinitriles and a Lewis acid.

Disclosed is a process for recovering diphosphonite-containing compounds from a feed mixture comprising diphosphonite-containing compounds, organic mononitriles, organic dinitriles and a Lewis acid in a multistage countercurrent liquid-liquid extractor with extraction solvent comprising aliphatic hydrocarbon, cycloaliphatic hydrocarbon or a mixture of aliphatic and cycloaliphatic hydrocarbon. The process comprises the steps of:

a) flowing the feed mixture to the first stage of the multistage countercurrent liquid-liquid extractor; and b) contacting the feed mixture with extraction solvent in the multistage countercurrent liquid-liquid extractor.

The first stage of the multistage countercurrent liquid-liquid extractor comprises a mixing section and a settling section. The mixing section provides a mixed phase comprising a light phase and a heavy phase. A light phase separates from a heavy phase in the settling section. A mixed phase comprising both heavy phase and light phase is present in the settling section between the light phase and the heavy phase. The light phase comprises extraction solvent and extracted diphosphonite-containing compounds. The heavy phase comprises organic mononitriles and organic dinitriles. At least a portion of the light phase is withdrawn from the settling section and treated to recover diphosphonite-containing compounds extracted into the light phase. At least a portion of the heavy phase is passed to the second stage of the multistage countercurrent liquid-liquid extractor.

The process further comprises at least one of the following additional steps, referred to herein as steps (i), (ii), (iii) and (iv).

Additional step (i) comprises withdrawing a portion of the heavy phase from the settling section of the first stage of the multistage countercurrent liquid-liquid extractor and recycling the withdrawn heavy phase to the settling section of the first stage of the multistage countercurrent liquid-liquid extractor. Of the five disclosures, which are combined in the present application, this additional step (i) is primarily described in WO 2014/205183 A1.

Additional step (ii) comprises withdrawing a portion of the light phase from the settling section of the first stage of the multistage countercurrent liquid-liquid extractor and recycling the withdrawn light phase to the mixing section of the first stage of the multistage countercurrent liquid-liquid extractor. Of the five disclosures, which are combined in the present application, this additional step (ii) is primarily described in WO 2014/205188 A1.

In additional step (iii), the first stage of the multistage countercurrent liquid-liquid extractor comprises a mixer-settler. Additional step (iii) comprises introducing a Lewis base into the settling section of the first stage. A complex of Lewis acid and Lewis base is formed in the settling section in the mixer-settler of the first stage. Of the five disclosures, which are combined in the present application, this additional step (iii) is primarily described in WO 2014/205190 A1.

Additional step (iv) comprises adding a polyamine to the mixing section of the first stage. Of the five disclosures, which are combined in the present application, this additional step (iv) is primarily described in WO 2014/205195 A1 and WO 2014/205337.

The mixing sections of the stages of the multistage counter current liquid-liquid extractor form an intimate mixture of unseparated light and heavy phase. This intimate mixture comprises an emulsion phase. The emulsion phase may or may not comprise particulate solid material. This emulsion phase separates into a light phase and a heavy phase in the settling sections of the stages, including the first stage. Accordingly, the settling sections of the stages will contain at least some emulsion phase located between the upper light phase and the lower heavy phase. This emulsion phase tends to reduce in size over time. However, in some instances settling takes longer than desired or the emulsion phase never fully separates into a light phase and a heavy phase. This separation problem may be particularly troublesome in the first stage of a multistage countercurrent liquid-liquid extractor.

Each of the above-described additional steps (i), (ii), (iii) and (iv) have been found to result in enhanced settling of the emulsion phase. For example, these additional steps may result in the reduction of the size of the emulsion phase in the settling section, wherein the size of the emulsion phase is based upon the size of the emulsion phase in the absence of additional step (i), (ii), (iii) or (iv). Enhanced settling in the settling section may also be measured as an increased rate of settling, based upon the rate of settling in the absence of additional step (i), (ii), (iii) or (iv).

Another problem, which may be solved by each of the above-described additional steps (i), (ii), (iii) and (iv), is formation of rag and build-up of a rag layer the settling section. Rag formation is discussed in U.S. Pat. No. 4,339,395 and U.S. Pat. No. 7,935,229. Rag comprises particulate solid material, and may be considered to be a form of an emulsion phase, which is particularly stable in the sense that it does not dissipate in a practical amount of time for conducting an extraction process. Rag may form in the mixing section or the settling section of an extraction stage, particularly the first stage of a multistage countercurrent liquid-liquid extractor. In the settling section, the rag forms a layer between the heavy phase and the light phase. The formation of a rag layer in the settling section inhibits proper settling of the heavy phase and the light phase. The formation of a rag layer may also inhibit the extraction of diphosphonite-containing compounds from the heavy phase into the light phase. In a worst case scenario, rag can build up to the extent of completely filling a separation section, necessitating shut down of the extraction process to clean out the settling section. It has been found that each of the above-described additional steps (i), (ii), (iii) and (iv) may reduce or eliminate the size of a rag layer or reduce its rate of formation, based upon the size and rate of formation of the rag layer in the absence of additional step (i), (ii), (iii) or (iv).

Accordingly, each of the above-described additional steps (i), (ii), (iii) and (iv) may achieve at least one of the following results: (a) a reduction in the size of an emulsion phase in the settling section, based upon the size of the emulsion phase in the absence of recycle of the heavy phase; (b) an increase in the rate of settling in the settling section, based upon the rate of settling in the absence of recycle of the heavy phase; (c) an increase in the amount of diphosphonite-containing compounds in the light phase, based upon the upon the amount of diphosphonite-containing compounds in the light phase in the absence of additional step (i), (ii), (iii) or (iv); (d) a partial or total reduction in the size of a rag layer in the settling section, based upon the size of a rag layer in the settling section in the absence of additional step (i), (ii), (iii) or (iv); and (e) reduction in the rate of formation of a rag layer in the settling section, based upon the rate of formation of a rag layer in the settling section in the absence of additional step (i), (ii), (iii) or (iv).

According to additional step (i), the second portion of the heavy phase, which is recycled in the first stage, may be recycled to the settling section in the absence of an intervening step to remove diphosphonite-containing compounds from the heavy phase.

According to additional step (i), the second portion of the heavy phase, which is recycled in the first stage, may be recycled to the settling section in the absence of passing through another liquid-liquid extraction stage.

The extraction solvent feed from the second stage of the multistage countercurrent liquid-liquid extractor to the first stage of the multistage countercurrent liquid-liquid extractor may comprise at least 1000 ppm, for example, from 2000 to 5000 ppm, of diphosphonite-containing compounds. The extraction solvent feed from the second stage may comprise at least 10 ppm, for example, from 20 to 200 ppm, of nickel.

According to additional step (i), a raffinate recycle ratio (RRR) may be between 0.1 and 0.9, for example, between 0.2 and 0.8, wherein RRR is defined by the ratio of X to Y, wherein X is the mass per unit time of the second portion of the heavy phase recycled to the settling section of the first stage of the multistage countercurrent liquid-liquid extractor, and wherein Y is the mass per unit time of all of the heavy phase withdrawn from the settling section of the first stage of the multistage countercurrent liquid-liquid extractor.

According to additional step (ii), an extraction solvent recycle ratio (ESRR) may be between 0.1 and 0.9, for example, between 0.2 and 0.8, wherein ESRR is defined by the ratio of X' to Y', wherein X' is the mass per unit time of the second portion of the light phase recycled to the mixing section of the first stage of the multistage countercurrent liquid-liquid extractor, and wherein Y' is the mass per unit time of all extraction solvent charged to the mixing section of the first stage of the multistage countercurrent liquid-liquid extractor.

At least a portion of the diphosphonite ligand may be complexed with zero valent Ni.

At least one stage of the extraction may be carried out above 40° C.

At least one stage of extraction may contain a Lewis base.

If at least one stage of extraction contains a Lewis base, the Lewis base may be a monodentate triarylphosphite or a monodentate triarylphosphine, wherein the aryl groups are unsubstituted or substituted with alkyl groups having 1 to 12 carbon atoms, and wherein the aryl groups may be interconnected.

The Lewis base may optionally be selected from the group consisting of:

a) anhydrous ammonia, pyridine, alkylamine, dialkylamine, trialkylamine wherein the alkyl groups have 1 to 12 carbon atoms; and b) polyamine.

If the Lewis base is a polyamine, the polyamine may comprise at least one selected from hexamethylene diamine, and dimers and trimers of hexamethylene diamine, for example, bis-hexamethylene triamine. It will be understood that a polyamine is a compound with at least two amino groups.

The Lewis base may optionally comprise a basic ion exchange resin, for example, Amberlyst 21® resin.

One example of a suitable cyclic alkane extraction solvent is cyclohexane.

At least a portion of the process may be carried out in an extraction column or a mixer-settler.

The feed mixture may be an effluent stream from a hydrocyanation process, for example, a process for hydrocyanating 3-pentenenitrile, a process for the single hydrocyanation of 1,3-butadiene to pentenenitriles or a process for the double hydrocyanation of 1,3-butadiene to adiponitrile.

The first stage of the multistage countercurrent liquid-liquid extractor may take place in an extraction column. The entire column may be considered to be a settling section comprising a mixing section between a heavy phase collection section and a light phase collection section. Heavy phase may be recycled to the mixing section of the extraction column.

The first stage of the multistage countercurrent liquid-liquid extractor may take place in a mixer-settler. The mixer-settler may comprise a settling section which is separate from the mixing section. Recycled heavy stream may be recycled to the settling section at a point upstream from the point of withdraw of the recycled heavy stream.

DETAILED DESCRIPTION OF THE INVENTION

The processes of the present invention involve methods for recovering diphosphonite-containing compounds from a mixture, which comprises diphosphonite-containing compounds and organic dinitriles, using liquid-liquid extraction.

Figure 1:
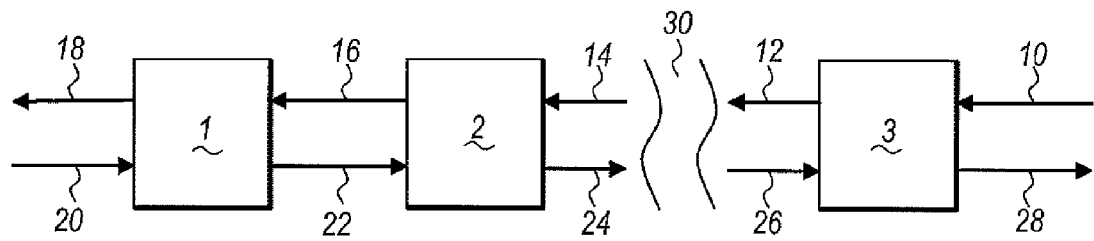
FIG. 1 is a diagram showing the flow of fluids through a multistage countercurrent liquid-liquid extractor.

FIG. 1 is a diagram of a multistage countercurrent liquid-liquid extractor. Lines in FIG. 1 represent flow of materials, rather than any particular type of equipment, such as pipes. Similarly, squares in this diagram represent stages or sections for mixing and settling, rather than any particular type of equipment.

Three stages are depicted in FIG. 1. The first stage is depicted by mixing and settling section 1. The second stage is depicted by mixing and settling section 2. The final stage is depicted by mixing and settling section 3. Gap 30 represents a space where additional stages may be inserted. For example, one or more, for example, from one to four, mixing and settling sections may be inserted in gap 30 between mixing and settling section 2 and mixing and settling section 3.

In FIG. 1, a fresh extraction solvent feed, for example, cyclohexane, is introduced into the multistage countercurrent extractor via line 10. The extraction solvent or light phase exiting from mixing and settling section 3 passes through line 12 to the next stage of the multistage extractor. In a multistage countercurrent liquid-liquid extractor having three stages, extraction solvent in line 12 would pass directly into stage 2 via line 14. Extraction solvent from stage 2 passes through line 16 to stage 1. The extraction solvent comprising extracted diphosphonite-containing compounds passes out of the stage 1 mixing and settling section through line 18.

A feed comprising diphosphonite-containing compounds is fed into the stage 1 mixer and settler via line 20. The feed further comprises a mixture comprising organic mononitriles and dinitriles, which is immiscible with the extraction solvent. In stage 1, a portion of the diphosphonite-containing compounds is extracted into the extraction solvent which exits stage 1 via line 18. The immiscible dinitrile and mononitrile mixture or the heavy phase is removed from the stage 1 mixing and settling section by line 22 and is passed into the stage 2 mixing and settling section. A portion of the diphosphonite-containing compounds is extracted into the light phase in the stage 2 mixing and settling section. The heavy phase exits the stage 2 mixing and settling section by line 24. Similarly, if there are additional stages in gap 30 shown in FIG. 1, extraction of diphosphonite-containing compounds will take place in such intermediate stages in a similar manner to that taking place in stage 2.

After the heavy phase passes through the first stage and any intermediate stages, it passes through the final stage mixing and settling section 3. In particular, the heavy phase is introduced into mixing and setting section 3 through line 26. After passing through the final stage mixing and settling section 3, the heavy phase exits via line 28.

A two-stage multistage countercurrent liquid-liquid extractor is represented in FIG. 1 by mixing and settling sections 1 and 2; lines 14, 16 and 18 showing the direction of extraction solvent flow; and lines 20, 22 and 24 showing the direction of heavy phase flow. In a two-stage multistage counter current liquid-liquid extractor, mixing and settling section 3; lines 10, 12, 26 and 28; and gap 30 are omitted. In the two stage countercurrent liquid-liquid extractor, extraction solvent comprising extracted diphosphonite-containing compounds passes from the extractor through line 18, and extracted heavy phase, i.e. raffinate, passes from the extractor through line 24.

Thus, it can be seen that the multistage countercurrent liquid-liquid extractor comprises two or more stages with countercurrent flow of extraction solvent and heavy phase.

Figure 2:
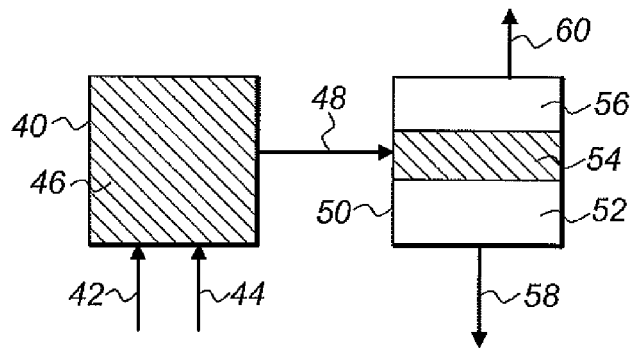
FIG. 2 is a diagram showing recycle of heavy phase in a settling section of a stage of a multistage countercurrent liquid-liquid extractor.

FIG. 2 is a diagrammatic representation of one type of a mixing and settling section, also referred to herein as a mixer-settler. This type of mixer-settler may be used in any of the stages shown in FIG. 1. This mixer-settler comprises a mixing section 40 and a settling section 50. The mixing section 40 and the settling section 50 are separate. All of the effluent from the mixing section 40 flows into the settling section 50. Fluid from the mixing section 40 flows through the settling section 50 in a horizontal manner, although there is also no restriction of movement of fluids vertically throughout the settling section 50.

An extraction solvent is introduced into the mixing section 40 by line 42. A feed comprising diphosphonite-containing compounds is introduced into the mixing section 40 by line 44. Alternatively, the contents of lines 42 and 44 may be combined upstream of the mixing section 40 and introduced into mixing section 40 through a single inlet. These two feeds are mixed in the mixing section 40 to provide a mixed phase comprising an emulsion phase represented in FIG. 2 by shaded area 46.

Line 48 represents the flow of mixed phase 46 from the mixing section 40 into the settling section 50. As depicted in FIG. 2, there are three phases in the settling section 50, including a heavy phase 52, a mixed phase 54, and a light phase 56. The heavy phase 52 is depleted in diphosphonite-containing compounds due to the extraction of diphosphonite-containing compounds into the light phase 56. Correspondingly, the light phase 56 is enriched in diphosphonite-containing compounds due to the extraction of diphosphonite-containing compounds into the light phase 56. Heavy phase 52 exits the settling section 50 via line 58. At least a portion of the light phase 56 is removed from the settling section 50 via line 60, and another portion of the light phase 56 may, optionally, be removed from the settling section 50 and recycled to mixing section 40 or settling section 50 through lines not shown in FIG. 2.

Although not shown in FIG. 2, which is diagrammatically shows the flow of fluids, it will be understood that each of the mixing section 40 and the settling section 50 may comprise one or more stages, subsections, compartments or chambers. For example, settling section 50 may include more than one chamber between the point of introduction of the mixed phase 46 through line 48 and the point of withdrawal of light phase and heavy phase through lines 58 and 60. Horizontal extension between the point of introduction of the mixed phase 46 through line 48 and the point of withdrawal of light and heavy phases through lines 58 and 60 promotes settling of the light and heavy phases 56 and 52. The size of the mixed phase 54 may become progressively smaller as fluids settle and flow through the chamber. For example, the final chamber from where fluids are removed may include little or no mixed phase 54. It will further be understood that mixing section 40 may include one or more types of mixing apparatus, such as an impeller, not shown in FIG. 2.

Figure 3:
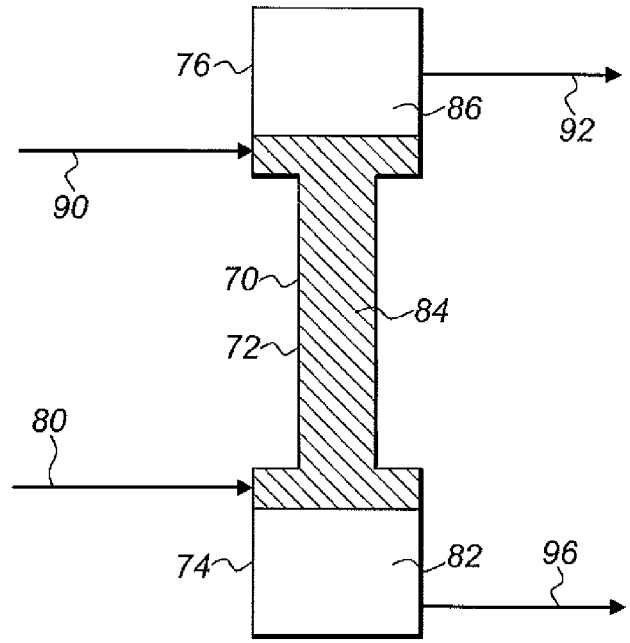
FIG. 3 is a diagram showing an extraction column.

FIG. 3 provides a representation of another type of apparatus for use as a mixing and settling section. The type of apparatus 70 shown in FIG. 3 is referred to herein as an extraction column. This extraction column 70 includes a mixing section 72, a heavy phase collection section 74 and a light phase collection section 76. The entire column 70 may be considered to be a settling section with a mixing section between collection section 74 and collection section 76. In extraction column 70 the mixing section 72 is part of the settling section. An extraction solvent is introduced into column 70 through line 80. A heavier phase comprising a diphosphonite-containing compound is introduced into column 70 through line 90. As the light phase passes upward through the column, and the heavy phase passes downward through the column, a mixture of the two phases is formed in mixing section 72. This mixture is represented in FIG. 3 as shaded mixed phase 84. This mixed phase 84 may comprise an emulsion phase. The point of introduction of heavy phase through line 90 should be sufficiently above the point of introduction of the light phase to allow for sufficient mixing of the two phases in the mixing section resulting in the extraction of diphosphonite-containing compounds into the light phase. The intimate mixing of light and heavy phase in mixing section 72 may be promoted by mechanical or static mixing apparatus not shown in FIG. 3. For example, mixing section 72 may comprise packing, baffles or perforated plates, not shown in FIG. 3.

The heavy phase 82 settles into collection section 74 and passes out of the column 70 through line 96. Light phase 86 settles in collection section 76 and passes from the column through line 92.

According to additional step (i), a portion of the heavy phase may be taken as a side stream from line 96 through a line not shown in FIG. 3 and passed into the mixing section 72 through line 90 or line 80 or a line not shown in FIG. 3 as recycle into column 70. Alternatively, a stream not shown in FIG. 3 may be taken directly from collection section 74, instead of as a side stream from line 96. In a particular embodiment, a stream from the heavy phase may flow directly into line 80 or into column 72 at a point near the interface of the mixed phase 84 and the heavy phase 82.

Recycle of heavy phase into the settling section of extraction column 70 increases the downward flow of heavy phase in the settling section. Without being bound by any theory, it is theorized that this increased downward flow may tend to breakup an emulsion phase, which may tend to otherwise form in the settling section. This emulsion phase, when present, may form at the interface of the mixed phase 84 and the heavy phase 82. Accordingly, the point of introduction of the recycled heavy phase should be sufficiently above to point where an emulsion phase would form to allow for heavy phase to flow downward through this point.

According to additional step (ii), a portion of the light phase may be taken as a side stream from line 92 through a line not shown in FIG. 3 and passed into the mixing section 72 through line 90 or line 80 or a line not shown in FIG. 3 as recycle into column 70. Alternatively, a stream not shown in FIG. 3 may be taken directly from collection section 76, instead of as a side stream from line 92. In a particular embodiment, a stream from the light phase may flow directly into line 80 or into column 72 at a point near the interface of the mixed phase 84 and the heavy phase 82.

Figure 4:
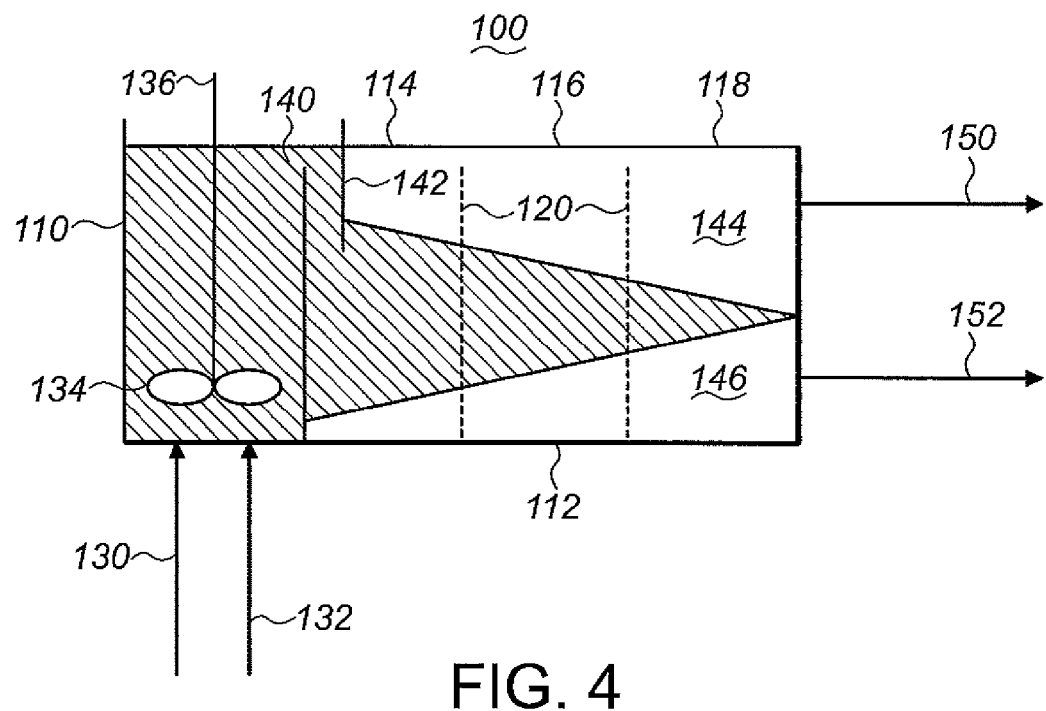
FIG. 4 is a diagram showing a settling section of a mixing/settling apparatus having three chambers in the settling section.

FIG. 4 provides a representation of a mixer-settler 100 having a multistage settling section. Mixer-settler 100 has a mixing section 110 and a settling section 112. In mixer-settler 100, the mixing section 110 is separate from the settling section 112. The settling section has three compartments, represented in FIG. 4 as sections 114, 116, and 118. These sections are separated by coalescence plates 120. The coalescence plates 120 may be designed to provide flow of separated light and heavy phases between chambers, while restricting the flow of emulsion phase between chambers. A feed comprising a diphosphonite-containing compound is passed into the mixing section 110 via line 130. The extraction solvent is introduced into mixing section 110 via line 132. The mixing section 110 includes an impeller 134 mounted on shaft 136 to provide for mechanical mixing of fluids. Mixing of the feeds provides a mixed phase comprising an emulsion phase represented in FIG. 4 by shading 140.

The mixed phase 140 flows into the settling section 112 as an overflow from the mixing section 110. This mixed phase 140 is prevented from flowing directly into the light phase 144 by baffle plate 142. As settling occurs in settling section 112, the mixed phase 140 decreases in volume, the volume of the light phase 144 increases, and the volume of the heavy phase 146 increases. Heavy phase 146 is removed from settling section 112, in particular from chamber 118, via line 152, and light phase 144 is removed from settling section 112, in particular, from chamber 118, via line 150.

According to additional step (i), a portion of the heavy phase may be removed through line 152 and taken as a side stream through a line not shown in FIG. 4 and introduced back into the settling section 112 at an appropriate point in section 114. The vertical point of introduction of line 154 into section 114 may be, for example, at or near the interface of the mixed phase 140 and the heavy phase 146.

Recycle of heavy phase 146 into the settling section increases the horizontal flow of heavy phase 146 relative to the horizontal flow of mixed phase 140 and light phase 144 through the settling section 112. Without being bound by any theory, it is theorized that by increasing flow of heavy phase 146 at the interface of the heavy phase 146 and the mixed phase 140 relative to the flow of the mixed phase 140 and the heavy phase 146, in general, the tendency of an emulsion phase to stabilize may be reduced. In particular, it is theorized that the increased horizontal flow of heavy phase 146 may result in mild agitation or shear at the interface of the heavy phase 146 and the mixed phase 140, where a stable emulsion phase might otherwise tend to form. It is also theorized that downward flow of heavy phase through an emulsion phase or rag layer may tend to force the emulsion phase or rag layer downward towards or into the heavy phase, thereby tending to break up the emulsion phase or rag layer.

It is desired to maximize the horizontal displacement of the point of withdraw and the point of reentry of the recycle stream. For example, in a multi-chamber settling section, heavy phase 146 may be removed from the chamber, e.g., chamber 118, furthest removed from the point of introduction of the mixed phase 146 from the mixing section 110 into the settling section 112, and the recycled heavy phase 146 may be reintroduced into the settling section 112 at a point near the introduction of the mixed phase 146 from the mixing section 110 into the settling section 112. For example, one point where the recycled heavy phase 146 may be introduced into the settling section 112 is at a point upstream of baffle plate 142, where mixed phase 140 overflows from the mixing section 110 into the settling section 112.

According to additional step (ii), a portion of the light phase removed through line 150 may be taken as a side stream through a line not shown in FIG. 4 and combined with the feed in line 132 as a source of extraction solvent feed to mixing section 110

It is desirable for both a mononitrile and a dinitrile to be present in the countercurrent contactor. For a discussion of the role of monodentate and bidentate ligand in extraction of hydrocyanation reactor effluent streams, see U.S. Pat. No. 3,773,809 to Walter and U.S. Pat. No. 6,936,171 to Jackson and McKinney.

For the process disclosed herein, suitable ratios of mononitrile to dinitrile components include 0.01 to 2.5, for example, 0.01 to 1.5, for example 0.65 to 1.5.

Maximum temperature is limited by the volatility of the hydrocarbon solvent utilized, but recovery generally improves as the temperature is increased. Examples of suitable operating ranges are 40° C. to 100° C. and 50° C. to 80° C.

The controlled addition of monophosphonite ligands may enhance settling. Examples of monophosphite ligands that may be useful as additives include those disclosed in Drinkard et al U.S. Pat. No. 3,496,215, U.S. Pat. No. 3,496,217, U.S. Pat. No. 3,496,218, U.S. Pat. No. 5,543,536, and published PCT Application WO 01/36429 (BASF).

The addition of Lewis base compounds to a mixture comprising diphosphonite-containing compounds, organic mononitriles and organic dinitriles may enhance settling, especially when the mixture comprises a Lewis acid, such as $ZnCl_2$. The addition may take place either before or during an extraction process in a multistage countercurrent extractor. Examples of suitable weak Lewis base compounds include water and alcohols. Suitable stronger Lewis base compounds include hexamethylene diamine, dimers and trimers of hexamethylene diamine, ammonia, aryl- or alkyl amines, such as pyridine or triethylamine, or basic resins such as Amberlyst 21®, a commercially available basic resin made by Rohm and Haas. The addition of Lewis base may reduce or eliminate any inhibiting effect of Lewis acid on catalyst recovery.

The diphosphonite-containing compounds extracted by the processes described herein are also referred to herein as bidentate phosphorus-containing ligands. These extracted ligands comprise free ligands (e.g., those which are not complexed to a metal, such as nickel) and those which are complexed to a metal, such as nickel. Accordingly, it will be understood that extraction processes described herein are useful for recovering diphosphonite-containing compounds which are metal/ligand complexes, such as a complex of zero valent nickel with at least one ligand comprising a bidentate-phosphorus containing ligand.

Diphosphonite Ligands

The diphosphonite-containing compound may be a diphosphonite ligand of formula (I):

$$(R^1)(R^2-O)P-O-Y-O-P(O-R^3)(R^4) \qquad \text{I}$$

where $R^1$ and $R^2$ are each independently identical or different, separate or bridged organic radicals; $R^3$ and $R^4$ are each independently identical or different, separate or bridged organic radicals; and Y is a bridging group.

The $R^1$ and $R^2$ radicals may each independently be identical or different organic radicals. Examples of $R^1$ and $R^2$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^3$ and $R^4$ radicals may each independently be identical or different organic radicals. Examples of $R^3$ and $R^4$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^1$ and $R^2$ radicals may each be separate or bridged. The $R^3$ and $R^4$ radicals may also each be separate or bridged. The $R^1$, $R^2$, $R^3$ and $R^4$ radicals may each be separate, two may be bridged and two separate, or all four may be bridged.

Examples of phosphonite-containing compounds of formula (I) may be diphosphonite ligands of formula (II) or (formula III):

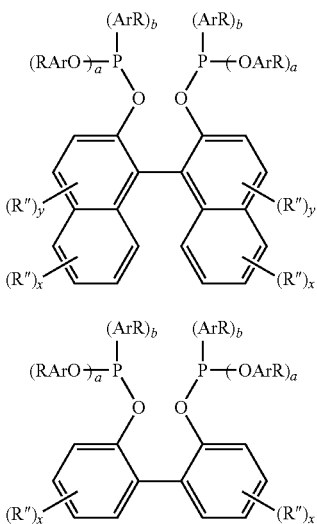

II

III

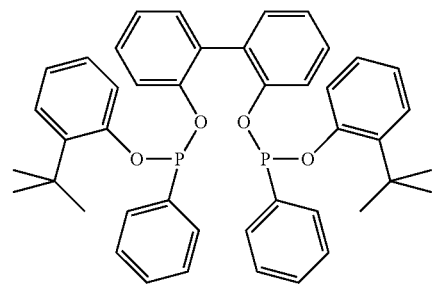

IV wherein:
x=0 to 4;
y=0 to 2;
a and b individually are either 0, 1, or 2, provided a+b=2;
each Ar is individually phenyl or naphthyl, and the two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide;
each R is individually hydrogen, ethenyl, propenyl, acryloyl, methacryloyl, an organic radical with a terminal ethenyl, propenyl, acryloyl, or methacryloyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;
each Ar can be further substituted with linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;
each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether.

At least one R in formula (II) or formula (III) may represent ethenyl, propenyl, acryloyl, methacryloyl or the organic radical with a terminal ethenyl, propenyl, acryloyl, or methacryloyl group and/or at least one R" may represent ethenyl, propenyl, or the organic radical with a terminal ethenyl or propenyl group.

An example of a diphosphonite ligand of formula (III) is a compound of formula (IV):

Diphosphonite ligands and the synthesis of these diphosphonite ligands are described in U.S. Pat. No. 6,924,345 and in U.S. Pat. No. 7,935,229.

Extraction Solvent

Suitable hydrocarbon extraction solvents include paraffins and cycloparaffins (aliphatic and alicyclic hydrocarbons) having a boiling point in the range of about 30° C. to about 135° C., including n-pentane, n-hexane, n-heptane and n-octane, as well as the corresponding branched chain paraffinic hydrocarbons having a boiling point within the range specified. Useful alicyclic hydrocarbons include cyclopentane, cyclohexane and cycloheptane, as well as alkyl substituted alicyclic hydrocarbons having a boiling point within the specified range. Mixtures of hydrocarbons may also be used, such as, for example, mixtures of the hydrocarbons noted above or commercial heptane which contains a number of hydrocarbons in addition to n-heptane. Cyclohexane is the preferred extraction solvent.

Recovery of Products

The lighter (hydrocarbon) phase recovered from the multistage countercurrent liquid-liquid extractor is directed to suitable equipment to recover catalyst, reactants, etc. for recycle to the hydrocyanation, while the heavier (lower) phase containing dinitriles recovered from the multistage countercurrent liquid-liquid extractor is directed to product recovery after removal of any solids, which may accumulate in the heavier phase. These solids may contain valuable components which may also be recovered, e.g., by the process set forth in U.S. Pat. No. 4,082,811.

The solids in the heavier phase, also referred to herein as the raffinate phase, may comprise a complex of Lewis acid and Lewis base (e.g., polyamine) in the form of dispersion of fine particles. The raffinate phase may also comprise extraction solvent, such as cyclohexane, pentenenitriles, which comprise 3-pentenenitrile, compounds with a higher boiling point than adiponitrile and compounds with a boiling point greater than the boiling point of pentenenitriles and less than the boiling point of adiponitrile. The complex of Lewis acid and Lewis base (e.g., polyamine) may be removed from the raffinate phase prior to removing extraction solvent, and especially before removing pentenenitriles from the raffinate phase.

The complex of Lewis acid and Lewis base may be removed by any customary solids removal process. Examples of such processes include filtration, crossflow filtration, centrifugation, sedimentation, classification and decantation. Common apparatus for such solids removal include filters, centrifuges and decanters.

It has been found that the complex of Lewis acid and Lewis base (e.g., polyamine) may catalyze the unwanted cyclization reaction of adiponitrile to form 2-cyanocyclopentylideneimine (CPI), especially when the raffinate phase is heated to temperatures used in the K'$_3$ column, discussed hereinafter, which is used to separate dinitriles, which comprise adiponitrile, from compounds having a boiling point higher than adiponitrile.

Figure 5:
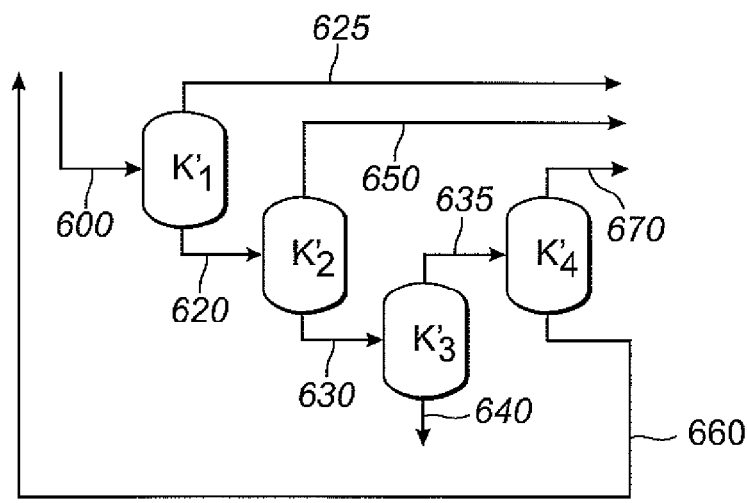
FIG. 5 is a diagram showing a distillation train which may be used to recover adiponitrile from a raffinate stream.

FIG. 5 shows a distillation train, which may be used as an adiponitrile purification section. FIG. 5 of the present disclosure corresponds to FIG. 3 of United States Patent Application Publication No. 2013/0211126. Line 600 transports a raffinate stream from an extraction zone into distillation column $K'_1$, where extraction solvent is separated from higher boiling components of the raffinate stream. In particular, extraction solvent, such as cyclohexane, is withdrawn from distillation column $K'_1$ through line 625, and higher boiling components of the raffinate stream are withdrawn from distillation column $K'_1$ through line 620.

The solvent-depleted stream in line 620 is then passed into distillation column $K'_2$, where pentenenitrile is separated from higher boiling components remaining in the raffinate stream. In particular, pentenenitrile, such as 3PN and any 2M3BN present, is withdrawn from distillation column $K'_2$ through line 650, and higher boiling components of the raffinate stream are withdrawn from distillation column $K'_2$ through line 630.

The pentenenitrile-depleted stream in line 630 is then passed into distillation column $K'_3$, where dinitriles are separated from higher boiling components remaining in the raffinate stream. In particular, dinitriles, such as ADN and MGN, are withdrawn from distillation column $K'_3$ through line 635, and higher boiling components of the raffinate stream are withdrawn from distillation column $K'_3$ through line 640. These higher boiling components in line 640 may comprise, for example, catalyst degradation products.

The dinitrile-enriched stream in line 635 is then passed into distillation column $K'_4$, where adiponitrile is separated from lower boiling dinitriles, such as MGN. In particular, MGN is withdrawn from distillation column $K'_4$ through line 670, and a purified adiponitrile stream is withdrawn from distillation column $K'_4$ through line 660.

Although not shown in FIG. 5, a complex of Lewis acid and Lewis base in the form of a dispersed solid precipitate may be removed, e.g., by filtration, from the raffinate before the stream is introduced into distillation column $K'_1$. According to another embodiment, this complex may be removed from the stream in line 620 before this stream enters distillation column $K'_2$. According to another embodiment, this complex may be removed from the stream in line 630 before this stream enters distillation column $K'_3$.

EXAMPLES

In the following examples, values for extraction coefficient are the ratio of weight fraction of catalyst in the extract phase (hydrocarbon phase) versus the weight fraction of catalyst in the raffinate phase (organonitrile phase). An increase in extraction coefficient results in greater efficiency in recovering catalyst. As used herein, the terms, light phase, extract phase and hydrocarbon phase, are synonymous. Also, as used herein, the terms, heavy phase, organonitrile phase and raffinate phase, are synonymous.

Analyses of the extract and the raffinate streams of the catalyst extraction were conducted on an Agilent 1100 series HPLC and via ICP. The HPLC was used to determine the extraction efficiency of the process.

In the Examples which follow, a diphosphite ligand is present. However, it is believed that the results of these Examples would be essentially the same if a diphosphonite ligand were substituted for the diphosphite ligand.

Examples 1-16 herein correspond to Examples 1-16 of WO 2014/205183. Examples 17 and 18 herein correspond to Examples 2 and 3 of WO 2014/205188. Examples 19-30 herein correspond to Examples 1-12 of WO 2014/205190. Examples 31-49 herein correspond to Examples 1-19 of WO 2014/205195. Examples 50-75 herein correspond to Examples 31-56 of WO 2014/205337.

Example 1

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. The extract from the second stage contained approximately 50 ppm nickel and 3100 ppm diphosphite ligand.

The reactor product was approximately:
85% by weight $C_6$ dinitriles
14% by weight $C_5$ mononitriles
1% by weight catalyst components
360 ppm by weight active nickel.

The laboratory reactor was then mixed at 1160 rotations-per-minute, for 20 minutes, and then allowed to settle for 15 minutes. After settling for 15 minutes, a stable emulsion was present throughout the extract phase. Samples were obtained of the extract and raffinate phases of the extractor and analyzed to determine the extent of catalyst extraction. The ratio of active nickel present in the extract phase vs. the raffinate phase was found to be 14.

Example 2

Using the same hydrocyanation reactor product and $2^{nd}$ stage settler extract as Example 1, a 50 mL, jacketed, glass laboratory extractor, equipped with a magnetic stirbar, digital stir-plate, and maintained at 65° C., was charged 10 grams of the product of a pentene-hydrocyanation reaction, and 10 grams of the extract from the second stage of a mixer-settler cascade, operated in counter-current flow.

The laboratory reactor was then mixed at 1160 rotations-per-minute, for 20 minutes, and then allowed to settle for 15 minutes. After settling for 15 minutes, a stable emulsion was present throughout the extract phase. Then, gentle mixing was applied, approximately 100 rpm, which caused the emulsion to disentrain. Samples were obtained of the extract and raffinate phases of the extractor and analyzed to determine the extent of catalyst extraction. The ratio of active nickel present in the extract phase vs. the raffinate phase was found to be 16.

Examples 1 and 2 illustrate the beneficial effect of applying gentle agitation to the heavy phase of the settling section of the first stage of a multistage countercurrent liquid-liquid extractor, and provide a practical simulation of the effect of recycle of the heavy phase in continuous operation.

TABLE 1

Catalyst and ligand extraction coefficient for various first stage extraction coefficient recycle ratios.

| Example | RRR | Catalyst Recovery (KLL) | Stable Emulsion |
| --- | --- | --- | --- |
| 1 | 0 | 14 | Yes |
| 2 | 1 | 16 | No |

KLL = amount of catalyst in the extract/amount of catalyst in the raffinate

Example 3

A three stage countercurrent liquid-liquid extractor, in continuous operation, utilizing the same two feed streams described in Example 1 was operated for a duration of 20 days. Samples were obtained of the extract and raffinate phases of the settling section of the extractor and analyzed to determine the extent of catalyst extraction. The ratio of active nickel present in the extract phase vs. the raffinate phase was found to be 5.6±2. A stable emulsion and rag was present throughout the extract portion of the settling section of the first stage of the extractor. The emulsion and rag was also present to a lesser extent in the settling sections of the second and third stages of the extractor.

Example 4

Example 3 was replicated except that the light-phase was recycled from the settling section back to the mixing section of the first stage of the countercurrent liquid-liquid extractor for a duration of 14 days. The benefits of this type of recycle of a light phase are described in an application identified as U.S. Published Application No. 2014/0350280. This Example 4 provides a base case for demonstrating improved results as described in Example 5 below.

The ratio of active nickel present in the extract phase vs. the raffinate phase was found to be 8.6±2. Less stable emulsion and rag was present throughout the extract portion of the settling section of the first stage of the extractor than in Example 3.

Example 5

Example 3 was replicated except that both light-phase and heavy-phase were recycled in the first stage of the countercurrent liquid-liquid extractor for a duration of 60 days. Recycle of the light phase took place from the settler to the mixer in the manner described in Example 4. Recycle of the heavy phase took place from the settler and back to the settler in a manner which provided mild agitation to the mixed phase in the settler.

The ratio of active nickel present in the extract phase vs. the raffinate phase was found to be 10.8±2. Less stable emulsion and rag was present throughout the extract portion of the settling section of the extractor than in Example 4.

Results of Examples 3-5 are summarized in Table 2.

TABLE 2

Catalyst extraction coefficients for continuous operation using phase recycles.

| Example | Duration (days) | Phase recycle | KLL | Stable emulsion |
|---|---|---|---|---|
| 3 | 20 | None | 5.6 ± 2 | Yes |
| 4 | 14 | Light | 8.6 ± 2 | No |
| 5 | 60 | Light and Heavy | 10.8 ± 2 | No |

Examples 3-5 illustrate the beneficial effect of recycling the light phase from the settler back to the mixer, and the heavy phase from the settler and back to the settler, of the settling section of the first stage of a multistage countercurrent liquid-liquid extractor while in continuous operation.

Example 6

Figure 6:
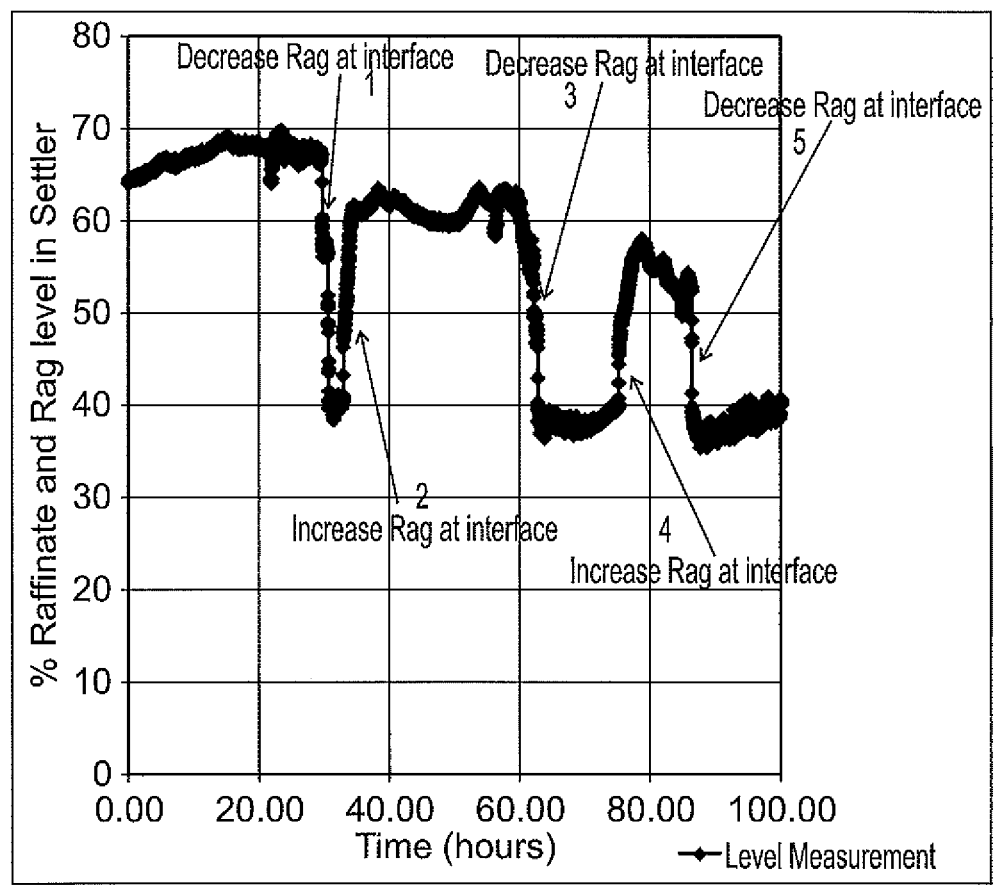
FIG. 6 is a graph showing the rag level in a settler during catalyst extraction in continuous operation.

Using the same countercurrent liquid-liquid extractor, in continuous operation as in Examples 3-5, the combined level of the raffinate and rag layers in the settling section of the extractor were measured by means of an RF probe (Universal III™ smart level). The data from the probe is shown in FIG. 6. A rapid change of >2% in less than 2 hour indicates that the rag layer was pushed into the raffinate layer, or the rag re-formed at the interface. When the raffinate recycle in the first stage, from the settler and back to the settler, disturbed the interface, the rag layer was pushed in the raffinate layer and the raffinate and rag layer total % level in the settler of the first stage decreases rapidly as shown in the FIG. 6. When the raffinate recycle no longer disturbed the interface, the rag layer again re-formed at the interface which was measured by the % level in the settler for the raffinate and rag increasing rapidly.

As shown in FIG. 6, the extraction was operated continuously for approximately 25 hours without raffinate recycle, and the rag level (including the thickness of the rag layer and the thickness of the underlying raffinate layer) was between 60% and 70%. After about 25 hours, recycle of raffinate was started. FIG. 6 shows that the rag level rapidly decreased to below 40% with a corresponding increase in the thickness of the extract layer. After about 1 hour, recycle of raffinate was discontinued, and, as shown in FIG. 6, the rag level rapidly increased to at least 60%. However, the rag level did not reach the rag level observed before the first recycle of raffinate. After the first recycle of raffinate was discontinued, the operation of the extraction was continued until the total elapsed time of the experiment reached about 60 hours. At that time, recycle of raffinate was resumed. FIG. 6 again shows that the rag level rapidly decreased to below 40% with a corresponding increase in the thickness of the extract layer. The recycle of raffinate was continued until the total elapsed time of the experiment reached about 77 hours. During this period, the rag level remained substantially constant below 40%. After about 77 hours of total elapsed time, the recycle of raffinate was again discontinued, and, as shown in FIG. 6, the rag level again rapidly increased, this time to a level between 50% and 60%. After about 85 hours of total elapsed time, recycle of raffinate was resumed again. FIG. 6 again shows that the rag level rapidly decreased to below 40%. This level was essentially maintained as recycle of raffinate continued until the end of the experiment at 100 hours of total elapsed time.

Examples 7-11

These Examples 7-11 illustrate that effective catalyst recovery occurs for a mononitrile to dinitrile ratio greater than 0.65.

Five different mixtures comprised of a Ni diphosphite complex, with the diphosphite ligand shown in Structure XX of U.S. Pat. No. 9,011,691 (where $R^{17}$ is isopropyl, $R^{18}$ is H, and $R^{19}$ is methyl), $ZnCl_2$ (equimolar with Ni) and differing in the ratio of mononitrile to dinitrile, were separately liquid-liquid batch extracted with an equal weight of cyane (i.e. cyclohexane). The molar ratio of organic mononitrile to organic dinitrile and the resulting extraction coefficients are shown in the Table 3 below. A compound may be effectively recovered if it has an extraction coefficient of 1 or greater at solvent to feed ratios greater than 1 using a countercurrent multistage extractor.

TABLE 3

Catalyst and ligand extraction coefficients for varying ratios of mononitriles-to-dinitriles

| Example | mononitrile/dinitrile | Catalyst extraction coefficient | Ligand extraction coefficient |
|---|---|---|---|
| 7 | 2.33 | 1.28 | 4.09 |
| 8 | 1.85 | 1.33 | 8.08 |
| 9 | 1.19 | 2.02 | 16.97 |
| 10 | 0.91 | 2.63 | 35.99 |
| 11 | 0.57 | 4.82 | 49.59 |

Example 12

This Example demonstrates the effect of hold-up time on the extractability of the diphosphite ligand catalyst.

A mixture comprised predominantly of organic dinitriles and a Ni diphosphite complex, the structure of the diphosphite ligand being shown in Structure XX of U.S. Pat. No. 9,011,691 (where $R^{17}$ is isopropyl, $R^{18}$ is H, and $R^{19}$ is methyl) and $ZnCl_2$ (equimolar with Ni) was divided into two portions. Both portions are liquid-liquid extracted in a three-stage contactor at 40° C., with an equal weight of cyclohexane. Both portions were sampled with time and the progress of the catalyst recovery into the extract phase is shown in Table 4 as the percent of the final steady state value achieved at a given time.

TABLE 4

Concentration of Diphosphite ligand with time in the extracting solvent phase.

| Time, minutes | % of steady state concentration at 40° C. |
|---|---|
| 2 | 12 |
| 4 | 19 |
| 8 | 34 |
| 14 | 52 |
| 30 | 78 |
| 60 | 100 |
| 91 | 100 |

Example 13

This Example illustrates the effect of temperature on the extractability of catalyst with last-stage extraction solvent recycle.

A mixture comprised predominantly of organic dinitriles and a Ni diphosphite complex, the structure of the diphosphite ligand being shown in Structure XXIV of U.S. Pat. No. 9,011,691 (where $R^{17}$ is methyl, $R^{18}$ is methyl and $R^{19}$ is H) and $ZnCl_2$ (equimolar with Ni) was divided into three portions. The portions were batch liquid-liquid extracted at 50° C., 65° C. and 80° C., respectively, with an equal weight of n-octane and monitored with time. The results are shown in Table 5.

TABLE 5

| Time | % of steady state at 50° C. | % of steady state at 65° C. | % of steady state at 80° C. |
|---|---|---|---|
| 2 | 0.0 | 0.0 | 1.8 |
| 4 | 0.0 | 0.0 | 1.6 |
| 8 | 0.0 | 0.0 | 3.6 |
| 14 | 0.0 | 0.0 | 4.3 |
| 20 | 0.0 | 0.0 | 3.6 |
| 30 | 0.0 | 0.0 | 7.6 |
| 60 | 0.0 | 1.6 | 16.3 |
| 90 | 0.7 | 4.0 | 48.6 |

Example 14

This Example demonstrates the effect of adding water in three-stage extraction with cyclohexane recycle in the first stage.

Fifteen grams of a mixture comprised predominantly of organic dinitriles and a Ni diphosphite complex, the structure of the diphosphite ligand being shown in Structure XXIV of U.S. Pat. No. 9,011,691 (where $R^{17}$ is methyl, $R^{18}$ is methyl and $R^{19}$ is H) and $ZnCl_2$ (equimolar with Ni), was extracted in a three-stage continuous extractor at a temperature of 50° C. with an equal weight of cyclohexane for one hour resulting in an catalyst extraction coefficient of 4.3.

To this mixture, 100 microliters of water was added. After continuing to heat and agitate for another hour, the diphosphite Ni extraction coefficient was measured as 13.4—a threefold increase.

Examples 15 and 16

These Examples demonstrate the effect of adding hexamethylene diamine (HMD) to the extraction zone.

Example 1 was repeated except that hexamethylene diamine was added to the product of a pentene-hydrocyanation reaction. To a 50 mL, jacketed, glass laboratory extractor, equipped with a magnetic stirbar, digital stir-plate, and maintained at 65° C., was charged 10 grams of the product of pentene-hydrocyanation reactor product, and 10 grams of the extract from the second stage of a mixer-settler cascade, operated in counter-current flow.

The reactor product was approximately:
85% by weight $C_6$ dinitriles
14% by weight $C_5$ mononitriles
1% by weight catalyst components
360 ppm by weight active nickel.

The laboratory reactor was then mixed at 1160 rotations-per-minute, for 20 minutes, and then allowed to settle for 15 minutes. A stable emulsion was present throughout the extract phase in the absence of the addition of HMD. After 15 minutes of settling, essentially no emulsion phase was present when HMD was added. Samples were obtained of the extract and raffinate phases of the extractor and analyzed to determine the extent of catalyst extraction. Results of Examples 1, 15 and 16 are summarized in Table 6.

TABLE 6

Effect of hexamethylene diamine on catalyst extraction

| Example | Concentration of HMD added (ppm) | Catalyst recovery (KLL) | Stable emulsion |
|---|---|---|---|
| 1 | 0 | 14 | Yes |
| 15 | 250 | 43 | No |
| 16 | 500 | 80 | No |

Example 17

Using the same hydrocyanation reactor product and 2$^{nd}$ stage settler extract as Example 1, a 50 mL, jacketed, glass laboratory extractor, equipped with a magnetic stirbar, digital stir-plate, and maintained at 65° C., was charged 5 grams of the product of a pentene-hydrocyanation reaction, and 15 grams of the extract from the second stage of a mixer-settler cascade, operated in counter-current flow.

The laboratory reactor was then mixed at 1160 rotations-per-minute, for 20 minutes, and then allowed to settle for 15 minutes. After settling for 15 minutes, no emulsion was present in the extractor. Samples were obtained of the extract and raffinate phases of the extractor and analyzed to determine the extent of catalyst extraction. The ratio of active nickel present in the extract phase vs. the raffinate phase was found to be 14.

Example 18

Using the same hydrocyanation reactor product and 2nd stage settler extract as Example 1, a 50 mL, jacketed, glass laboratory extractor, equipped with a magnetic stirbar, digital stir-plate, and maintained at 65° C., was charged 6 grams of the product of a pentene-hydrocyanation reaction, and 12 grams of the extract from the second stage of a mixer-settler cascade, operated in counter-current flow.

The laboratory reactor was then mixed at 1160 rotations-per-minute, for 20 minutes, and then allowed to settle for 15 minutes. After settling for 15 minutes, no emulsion was present in the extractor. Samples were obtained of the extract and raffinate phases of the extractor and analyzed to determine the extent of catalyst extraction. The ratio of active nickel present in the extract phase vs. the raffinate phase was found to be 18.

Examples 1, 17 and 18 illustrate the beneficial effect of increasing extract-to-dinitrile ratio on the extraction, and provide a practical simulation of the effect of recycle of the light phase in continuous operation. Results are summarized in Table 7.

TABLE 7

Catalyst and ligand extraction coefficient for various final stage extraction coefficient recycle ratios.

| Example | ESRR | Catalyst Recovery (KLL) | Stable Emulsion |
|---|---|---|---|
| 1 | 0 | 14 | Yes |
| 17 | 0.5 | 14 | No |
| 18 | 0.7 | 18 | No |

Example 19

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. The extract from the second stage contained approximately 50 ppm nickel and 3100 ppm diphosphite ligand. No additives were present.

The reactor product was approximately:
85% by weight $C_6$ dinitriles
14% by weight $C_5$ mononitriles
1% by weight catalyst components
420 ppm by weight active nickel
566 ppm by weight zinc.

The laboratory reactor was then mixed at 1160 rotations-per-minute, for 20 minutes, and then allowed to settle for 15 minutes. After settling for 15 minutes, a stable emulsion was present throughout the extract phase. Samples were obtained of the extract and raffinate phases of the extractor and analyzed to determine the extent of catalyst extraction. The ratio of active nickel present in the extract phase vs. the raffinate phase was found to be 14. The concentration of zinc in the raffinate was 566 ppm.

Example 20

Example 19 was repeated except that 500 ppm of polyethylenimine (PEI) was added to the system. The polyethylenimine (PEI) was end-capped with ethylenediamine and had an average Mn~600.

Example 21

Example 19 was repeated except that 1000 ppm of polyethylenimine (PEI) was added to the system. The polyethylenimine (PEI) was end-capped with ethylenediamine and had an average Mn~600.

Example 22

Example 19 was repeated except that 500 ppm of polyethylenimine, aqueous solution (PEI/$H_2$O) was added to the system. The polyethylenimine, aqueous solution was a polyethylenimine solution in water having a PEI/$H_2$O ratio of 1:1. The polyethyleneimine had an average Mn~1200.

Example 23

Example 19 was repeated except that 1000 ppm of polyethylenimine, aqueous solution (PEI/$H_2$O) was added to the system. The polyethylenimine, aqueous solution was a polyethylenimine solution in water having a PEI/$H_2$O ratio of 1:1. The polyethyleneimine had an average Mn~1200.

Example 24

Example 19 was repeated except that 1000 ppm of polyacrylate, sodium was added to the system. The polyacrylate, sodium was poly(acrylic acid) sodium salt with an average Mw~2100.

Example 25

Example 19 was repeated except that 3000 ppm of polyacrylate, sodium was added to the system. The polyacrylate, sodium was poly(acrylic acid) sodium salt with an average Mw~2100.

Example 26

Example 19 was repeated except that 500 ppm of a surfactant was added to the system. The surfactant was an aqueous solution of mixture of an alkyldimethylamide, an alkylethersulfate, and an alkylphosphateester.

Example 27

Example 19 was repeated except that 1000 ppm of a surfactant was added to the system. The surfactant was an aqueous solution of mixture of an alkyldimethylamide, an alkylethersulfate, and an alkylphosphateester.

Example 28

Example 19 was repeated except that 250 ppm of hexamethylene diamine (HMD) was added to the system.

Example 29

Example 19 was repeated except that 500 ppm of hexamethylene diamine (HMD) was added to the system.

Example 30

Example 19 was repeated except that 1000 ppm of hexamethylene diamine (HMD) was added to the system.

Results of Examples 19-30 are summarized in Table 8. The data summarized in Table 1 represent evaluations of a number of additives for prevention of formation of stable emulsions and rags during catalyst extraction. Example 19 is a control experiment, which shows that in the absence of any additive a stable emulsion is formed. Examples 20-21 show that PEI is ineffective for preventing formation of a stable emulsion under these conditions. Example 22 shows that 1:1 polyethylenimine in water is ineffective for preventing stable emulsion formation at 500 ppm. By way of contrast, Example 23 shows that PEI/H$_2$O is effective at 1000 ppm for preventing stable emulsion formation. Examples 24-25 show that polyacrylate, sodium salt, is not effective at 1000 ppm, but is at 3000 ppm loading. Examples 26-27 show that the surfactant solution is not effective under any of the conditions evaluated for prevention of a stable emulsion. Examples 28-30 show that hexamethylene diamine is effective under these conditions for prevention of formation of a stable emulsion during catalyst extraction over the range of concentrations from 250-1000 ppm.

TABLE 8

Effectiveness of additives for prevention of stable emulsion formation during catalyst extraction

| Example | Additive | Concentration (ppm) | Stable emulsion |
|---|---|---|---|
| 19 | None | 0 | Yes |
| 20 | PEI | 500 | Yes |
| 21 | PEI | 1000 | Yes |
| 22 | PEI/H$_2$O (1:1) | 500 | Yes |
| 23 | PEI/H$_2$O (1:1) | 1000 | No |
| 24 | Polyacrylate, sodium | 1000 | Yes |
| 25 | Polyacrylate, sodium | 3000 | No |
| 26 | Surfactant | 500 | Yes |
| 27 | Surfactant | 1000 | Yes |
| 28 | HMD | 250 | No |
| 29 | HMD | 500 | No |
| 30 | HMD | 1000 | No |

Example 31

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. This extract from the second stage comprised approximately 50 ppm nickel and 3100 ppm diphosphite ligand. The hexamethylene diamine concentration in the system was 0 ppm.

The reactor product was approximately:
85% by weight C$_6$ dinitriles
14% by weight C$_5$ mononitriles
1% by weight catalyst components
200 ppm by weight active nickel
230 ppm by weight zinc.

The laboratory reactor was then mixed at 500 rotations-per-minute, for 10 minutes, and then allowed to settle for 1 minute. After settling for 1 minute, a stable emulsion was present throughout the extract phase. Samples were obtained of the extract and raffinate phases of the extractor and analyzed to determine the extent of catalyst extraction. The ratio of active nickel present in the extract phase vs. the raffinate phase was found to be 5. The concentration of zinc in the raffinate was found to be 230 ppm.

Example 32

Example 31 was repeated except that hexamethylene diamine (HMD) was added to the system. In particular, a sufficient amount of HMD was added so that the molar ratio of Zn/HMD was 12 in the system.

Example 33

Example 31 was repeated except that hexamethylene diamine (HMD) was added to the system. In particular, a sufficient amount of HMD was added so that the molar ratio of Zn/HMD was 6 in the system.

Example 34

Example 31 was repeated except that hexamethylene diamine (HMD) was added to the system. In particular, a sufficient amount of HMD was added so that the molar ratio of Zn/HMD was 2.4 in the system.

Example 35

Example 31 was repeated except that hexamethylene diamine (HMD) was added to the system. In particular, a sufficient amount of HMD was added so that the molar ratio of Zn/HMD was 1.2 in the system.

Example 36

Example 31 was repeated except that bis-hexamethylene triamine (BHMT) was added to the system. In particular, a sufficient amount of BHMT was added so that the molar ratio of Zn/BMHT was 5.9 in the system.

Example 37

Example 31 was repeated except that bis-hexamethylene triamine (BHMT) was added to the system. In particular, a sufficient amount of BHMT was added so that the molar ratio of Zn/BMHT was 2.9 in the system.

Example 38

Example 31 was repeated except that bis-hexamethylene triamine (BHMT) was added to the system. In particular, a sufficient amount of BHMT was added so that the molar ratio of Zn/BMHT was 1.2 in the system.

Example 39

Example 31 was repeated except that bis-hexamethylene triamine (BHMT) was added to the system. In particular, a sufficient amount of BHMT was added so that the molar ratio of Zn/BMHT was 12 in the system.

Example 40

Example 31 was repeated except that 1,2-diaminocyclohexane (DCH) was added to the system. In particular, a sufficient amount of DCH was added so that the molar ratio of Zn/DCH was 1.6 in the system.

Example 41

Example 31 was repeated except that 1,2-diaminocyclohexane (DCH) was added to the system. In particular, a sufficient amount of DCH was added so that the molar ratio of Zn/DCH was 2 in the system.

Example 42

Example 31 was repeated except that 1,2-diaminocyclohexane (DCH) was added to the system. In particular, a sufficient amount of DCH was added so that the molar ratio of Zn/DCH was 4 in the system.

Example 43

Example 31 was repeated except that 1,2-diaminocyclohexane (DCH) was added to the system. In particular, a sufficient amount of DCH was added so that the molar ratio of Zn/DCH was 8 in the system.

Example 44

Example 31 was repeated except that triethylamine (TEA) was added to the system. In particular, a sufficient amount of TEA was added so that the molar ratio of Zn/TEA was 1 in the system.

Example 45

Example 31 was repeated except that octylamine was added to the system. In particular, a sufficient amount of octylamine was added so that the molar ratio of Zn/octylamine was 1.3 in the system.

Example 46

Example 31 was repeated except that polyethyleneglycol (PEG-600) was added to the system. In particular, a sufficient amount of PEG-600 was added so that the molar ratio of Zn/PEG-600 was 1.5 in the system.

Example 47

Example 31 was repeated except that adipamide was added to the system. In particular, a sufficient amount of adipamide was added so that the molar ratio of Zn/adipamide was 2.3 in the system.

Example 48

Example 31 was repeated except that triphenyl phosphine ($Ph_3P$) was added to the system. In particular, a sufficient amount of $Ph_3P$ was added so that the molar ratio of $Zn/Ph_3P$ was 1 in the system.

Example 49

Example 31 was repeated except that calcium hydroxide ($Ca(OH)_2$) was added to the system. In particular, a sufficient amount of $Ca(OH)_2$ was added so that the molar ratio of $Zn/Ca(OH)_2$ was 0.3 in the system.

Results of Examples 31-49 are summarized in Table 1.

TABLE 9

| Ex./CEx. | Temp (° C.) | Time (min) | Zn/Additive | Additive | KLL | Zn/Ni |
|---|---|---|---|---|---|---|
| 31 | 65 | 10 |  | None | 5 | 1.15 |
| 32 | 65 | 10 | 12.0 | HMD | 13 | 1.09 |
| 33 | 65 | 10 | 6.0 | HMD | 13 | 1.11 |
| 34 | 65 | 10 | 2.4 | HMD | 23 | 0.43 |
| 35 | 65 | 10 | 1.2 | HMD | 84 | 0.12 |
| 36 | 65 | 10 | 5.9 | BHMT | 102 | 0.12 |
| 37 | 65 | 10 | 2.9 | BHMT | 80 | 0.17 |
| 38 | 65 | 10 | 1.2 | BHMT | 112 | 0.17 |
| 39 | 65 | 10 | 12.0 | BHMT | 18 |  |
| 40 | 65 | 10 | 1.6 | DCH | 119 | 0.85 |
| 41 | 65 | 10 | 2 | DCH | 114 |  |
| 42 | 65 | 10 | 4 | DCH | 27 | 1.03 |
| 43 | 65 | 10 | 8 | DCH | 8 | 1.05 |
| 44 | 65 | 10 | 1 | TEA | 20 | 0.94 |
| 45 | 65 | 10 | 1.3 | Octylamine | 63 | 0.96 |
| 46 | 65 | 10 | 1.5 | PEG-600 | 5 | 1.07 |
| 47 | 65 | 10 | 2.3 | Adipamide | 6 |  |
| 48 | 65 | 10 | 1 | $Ph_3P$ | 4 | 1.15 |
| 49 | 65 | 10 | 0.3 | $Ca(OH)_2$ | 14 |  |

KLL = amount of catalyst in the extract/amount of catalyst in the raffinate; Zn/Additive = the molar ratio of the zinc-to-additive during extraction; Zn/Ni = the ratio of the total amount of zinc-to-nickel remaining in both phases after the extraction, as determined by inductively coupled plasma spectrometry (ICP).

The data summarized in Table 9 represent evaluations of a number of materials as potential additives for improved catalyst extraction. Examples 31-35 show the beneficial effect of hexamethylene diamine (HMD) on catalyst extraction, as the HMD loading increases (represented by decreasing Zn/Additive ratio) the catalyst extraction efficiency (represented by KLL) increases. Examples 36-39 show the beneficial effect of bis-hexamethylene triamine (BHMT) on catalyst extraction. Examples 40-43 show the beneficial effect of 1,2-diaminocyclohexane (DCH) on catalyst extraction. Example 45 shows the beneficial effect of adding octylamine on catalyst extraction. Example 49 shows the beneficial effect of calcium hydroxide on catalyst extraction. By way of contrast, Examples 46-48 show little effect on catalyst extraction using PEG-600, adipamide, and triphenyl phosphine, respectively.

Examples 50-55

These Examples demonstrate the beneficial effect of adding hexamethylene diamine (HMD) on the reaction temperature required for catalyst extraction. For Examples 50-52, Example 31 was repeated, but the mixing time was 20 minutes, and the temperature was varied as indicated in Table 10. For Examples 53-55, Example 35 was repeated, and the temperature was varied as indicated in Table 10.

TABLE 10

Effect of hexamethylene diamine on temperature for catalyst extraction.

| Example | Temp (° C.) | KLL | Zn/HMD |
|---|---|---|---|
| 50 | 65 | 16.76 | No HMD |
| 51 | 55 | 13.25 | No HMD |
| 52 | 45 | 8.06 | No HMD |
| 53 | 65 | 84.42 | 1.2 |
| 54 | 55 | 82.91 | 1.2 |
| 55 | 45 | 82.00 | 1.2 |

The data summarized in Table 10 represent evaluations of catalyst extraction performed at varying temperature from 45 to 65 degrees Celsius, with and without HMD present. Examples 50-52 show that catalyst extraction increases linearly with increasing temperature (represented by KLL). Examples 53-55 show that catalyst extraction does not require increased temperature when HMD added.

Examples 56-63

These Examples demonstrate the beneficial effect of adding hexamethylene diamine (HMD) on the mixing time required for catalyst extraction. For Examples 56-59, Example 50 was repeated, and the mixing time was varied as indicated in Table 11. For Examples 60-63, Example 35 was repeated, and the mixing time was varied as indicated in Table 11.

TABLE 11

Effect of hexamethylene diamine on mixing time required for catalyst extraction.

| Example | Mixing Time | KLL | Zn/HMD |
|---|---|---|---|
| 56 | 20 | 16.13 | No HMD |
| 57 | 10 | 14.86 | No HMD |
| 58 | 5 | 14.49 | No HMD |
| 59 | 1 | 11.05 | No HMD |
| 60 | 10 | 84.42 | 1.2 |
| 61 | 5 | 114.34 | 1.2 |
| 62 | 1 | 98.24 | 1.2 |
| 63 | 0.5 | 56.23 | 1.2 |

The data summarized in Table 11 represent evaluations of catalyst extraction performed at varying mixing time from 20 minutes to 30 seconds, with and without HMD present. Examples 55-59 show that a decrease in catalyst extraction occurs when the mixing time is decreased to less than 5 minutes. Examples 60-63 show that catalyst extraction does not decrease until the mixing time is decreased to less than 1 minute, when HMD added.

Examples 64-67

These Examples demonstrate the beneficial effect of adding hexamethylene diamine (HMD) and bis-hexamethylene triamine (BHMT) to the mixing section of a mixer-settler, rather than to the feed line to this mixing section. Results are shown in Table 12.

TABLE 12

Effect of additive addition point.

| Example | Addition Point | Additive | Mixing Time | KLL | Stable Emulsion |
|---|---|---|---|---|---|
| 64 | Mixer | HMD | 20 | 23 | No |
| 65 | Mixer | BHMT | 20 | 80 | No |
| 66 | Feed Line | HMD | N/A | 14 | Yes |
| 67 | Feed Line | BHMT | N/A | 14 | Yes |

Examples 64-67 show that addition of the additives HMD or BHMT directly to the mixer system of a catalyst extraction system causes a beneficial increase in catalyst recovery, as indicated by increased KLL.

Examples 68-72

These Examples demonstrate the ability of complex of zinc chloride ($ZnCl_2$) and bis-hexamethylene triamine (BHMT) to catalyze the cyclization of adiponitrile (ADN) to 2-cyanocyclopentylideneimine (CPI) under conditions encountered when a raffinate stream is refined to produce purified ADN.

A simulated raffinate composition which was obtained from the tails stream of a column for removal of pentenenitriles from dinitriles (i.e. column $K'_2$ and stream 630 in FIG. 5) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 13.

TABLE 13

Amount of additive.

| Example | Additive | Amount of BHMT | Zn/BHMT |
|---|---|---|---|
| 68 | BHMT + $ZnCl_2$ | 1 wt % | 1 |
| 69 | BHMT + $ZnCl_2$ | 2 wt % | 0.5 |
| 70 | BHMT + $ZnCl_2$ | 0.5 wt % | 2 |
| 71 | BHMT | 2 wt % | N/A |
| 72 | $ZnCl_2$ | 0 | N/A |

In Table 13, it will be understood that the amount of BHMT is based on the total weight of the raffinate composition before addition of the additive. It will be further understood that the ratio of Zn/BHMT is expressed in terms of equivalents of Zn per mole of BHMT. The amount of $ZnCl_2$ added as per Example 72 (EX 72) was 3 wt %, based on the total weight of the raffinate composition before addition of the $ZnCl_2$.

After the addition of the additive, samples of the mixture were taken at 1 hour, 2 hours, 3 hours and 5 hours. These samples were analyzed, and the concentration of CPI in the samples was determined in terms of CPI (mol/L), i.e. moles of CPI per liter of the mixture. Results are shown in FIG. 7.

Figure 7:
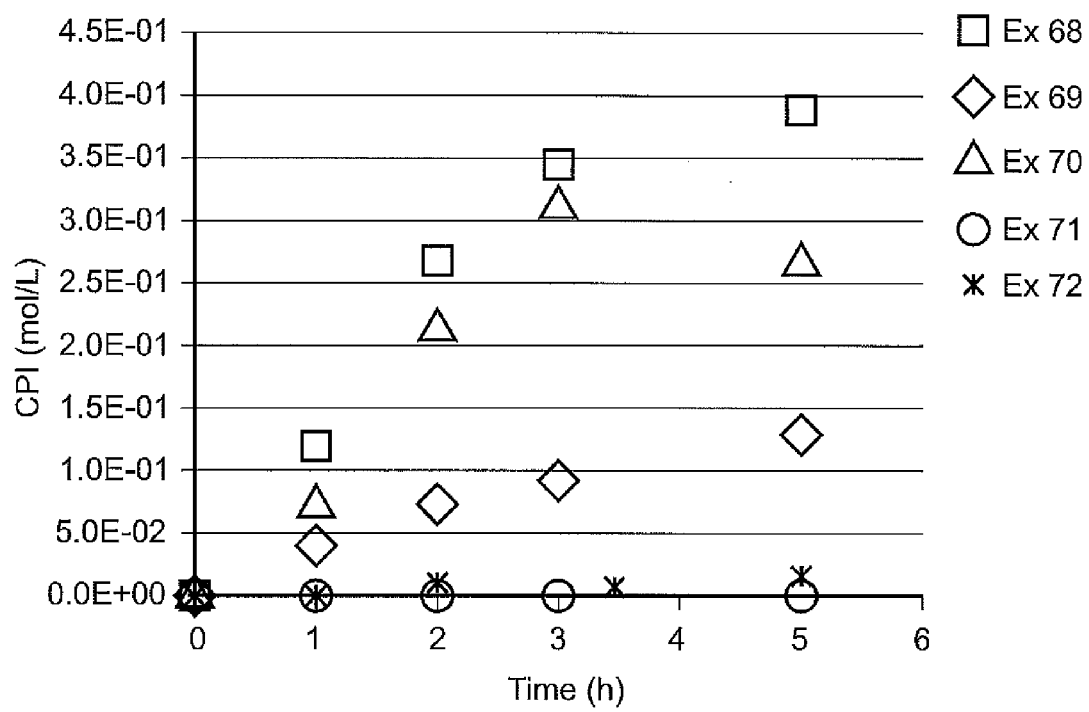
FIGS. 7 and 8 are graphs showing the conversion of adiponitrile to 2-cyanocyclopentylideneimine (CPI) in the presence of various additives over time.

FIG. 7 shows that CPI formation was negligible according to Example 71 (EX 71), wherein the additive included BHMT in the absence of $ZnCl_2$. FIG. 7 also shows that CPI formation was negligible according to Example 72 (EX 72), wherein the additive included $ZnCl_2$ in the absence of BHMT. However, FIG. 7 shows that considerable amounts of 2-cyanocyclopentylideneimine (CPI) were formed according to Examples 68-70 (EX 68 to EX 70) in increasing quantities over time when the additive included both BHMT and ZnCl$_2$.

Examples 73-75

These Examples demonstrate the ability of a complex of zinc chloride (ZnCl$_2$) and hexamethylene diamine (HMD) to catalyze the cyclization of adiponitrile (ADN) to 2-cyano-cyclopentylideneimine (CPI) under conditions encountered when a raffinate stream is refined to produce purified ADN.

A raffinate material which was obtained from the tails stream of a column for removal of pentenenitriles from dinitriles (i.e. column K'$_2$ and stream 630 in FIG. 5) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 14.

TABLE 14

| | Amount of additive. | | |
|---|---|---|---|
| Example | Additive | Amount of HMD | Zn/HMD |
| 73 | HMD + ZnCl$_2$ | 0.5 wt % | 1 |
| 74 | ZnCl$_2$ | 0 | N/A |
| 75 | HMD | 0.5 wt % | N/A |

In Table 14 it will be understood that the amount of HMD is based on the total weight of the raffinate composition before addition of the additive. It will be further understood that the ratio of Zn/HMD is expressed in terms of equivalents of Zn per mole of HMD. The amount of ZnCl$_2$ added as per Example 74 (EX 74) was 0.6 wt %, based on the total weight of the raffinate composition before addition of the ZnCl$_2$.

After the addition of the additive, samples of the mixture were taken at various times including 1 hour, 2 hours, 3 hours, 3.5 hours and 5 hours. These samples were analyzed, and the concentration of CPI in the samples was determined in terms of CPI (mol/L), i.e. moles of CPI per liter of the mixture. Results are shown in FIG. 8.

Figure 8:
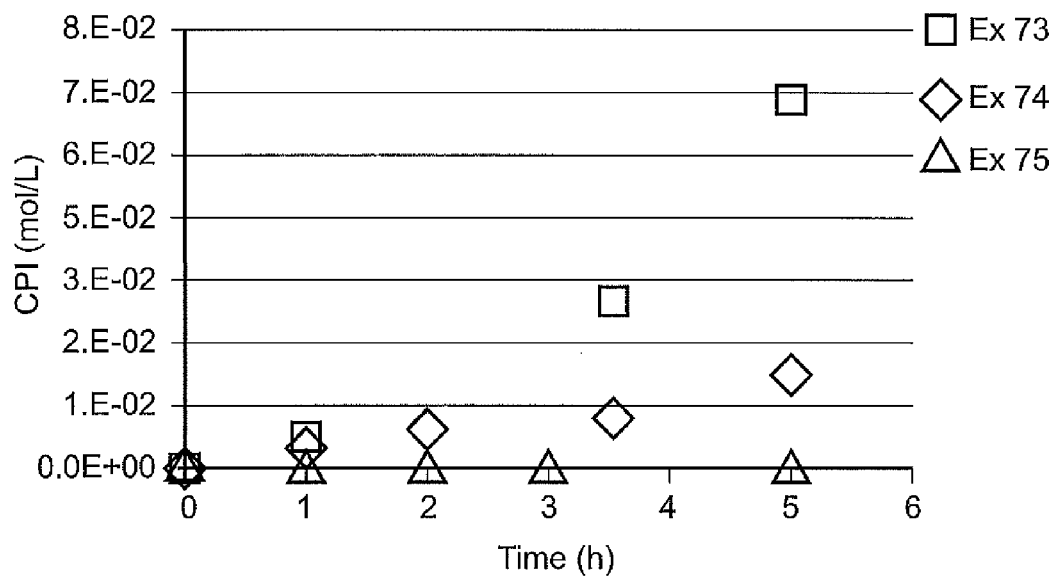

FIG. 8 shows that CPI formation was negligible according to Example 75 (EX 75), wherein the additive included HMD in the absence of ZnCl$_2$. FIG. 8 also shows that only small amounts of CPI were formed according to Example 74 (EX 74), wherein the additive included ZnCl$_2$ in the absence of HMD. However, FIG. 8 shows that considerable amounts of 2-cyanocyclopentylideneimine (CPI) were formed according to Example 73 (EX 73) in increasing quantities over time when the additive included both HMD and ZnCl$_2$, especially when the mixture was heated for 3.5 and 5 hours.

What is claimed is:

1. A process for recovering diphosphonite-containing compounds from a feed mixture comprising diphosphonite-containing compounds, organic mononitriles, organic dinitriles and a Lewis acid in a multistage countercurrent liquid-liquid extractor with extraction solvent comprising aliphatic hydrocarbon, cycloaliphatic hydrocarbon or a mixture of aliphatic and cycloaliphatic hydrocarbon, said process comprising:
a) flowing the feed mixture to the first stage of the multistage countercurrent liquid-liquid extractor; and
b) contacting the feed mixture with extraction solvent in the multistage countercurrent liquid-liquid extractor, wherein the multistage countercurrent liquid-liquid extractor comprises at least 2 stages, wherein each stage of the multistage countercurrent liquid-liquid extractor comprises a mixing section and a settling section, wherein the mixing section provides a mixed phase comprising a light phase and a heavy phase, wherein a light phase separates from a heavy phase in the settling section, wherein a mixed phase, which comprises both a heavy phase and a light phase, is present in the settling section between the light phase and the heavy phase, wherein the light phase comprises extraction solvent and extracted diphosphonite-containing compounds, wherein the heavy phase comprises organic mononitriles and organic dinitriles, wherein at least a portion of the light phase is withdrawn from the settling section of the first stage and treated to recover diphosphonite-containing compounds extracted into the light phase, wherein at least a portion of the heavy phase from the first stage is passed to the second stage of the multistage countercurrent liquid-liquid extractor, wherein fresh extraction solvent is fed to the final stage, wherein light phase from the second stage is fed to the first stage, and wherein the process further comprises at least one of the following additional steps:
   (i) withdrawing a portion of the heavy phase from the settling section of the first stage of the multistage countercurrent liquid-liquid extractor and recycling the withdrawn heavy phase to the settling section of the first stage of the multistage countercurrent liquid-liquid extractor; or
   (ii) withdrawing a portion of the light phase from the settling section of the first stage of the multistage countercurrent liquid-liquid extractor and recycling the withdrawn light phase to the mixing section of the first stage of the multistage countercurrent liquid-liquid extractor.

2. The process of claim 1, wherein a portion of the heavy phase is withdrawn from the settling section of the first stage of the multistage countercurrent liquid-liquid extractor and recycled to the settling section of the first stage of the multistage countercurrent liquid-liquid extractor, wherein a raffinate recycle ratio (RRR) is between 0.1 and 0.9, wherein RRR is defined by the ratio of X to Y, wherein X is the mass per unit time of the portion of the heavy phase recycled to the settling section of the first stage of the multistage countercurrent liquid-liquid extractor, and wherein Y is the mass per unit time of all of the heavy phase withdrawn from the settling section of the first stage of the multistage countercurrent liquid-liquid extractor.

3. The process of claim 2, wherein the RRR is between 0.2 and 0.8.

4. The process of claim 1, wherein at least one stage of the extraction is carried out above 40° C.

5. The process of claim 1, wherein a portion of the light phase is withdrawn from the settling section of the first stage of the multistage countercurrent liquid-liquid extractor and recycled to the mixing section of the first stage of the multistage countercurrent liquid-liquid extractor, wherein an extraction solvent recycle ratio (ESRR) is between 0.1 and 0.9, wherein ESRR is defined by the ratio of X' to Y', wherein X' is the mass per unit time of the portion of the light phase recycled to the mixing section of the first stage of the multistage countercurrent liquid-liquid extractor, and wherein Y' is the mass per unit time of all extraction solvent charged to the mixing section of the first stage of the multistage countercurrent liquid-liquid extractor.

6. The process of claim 5, wherein the ESRR is between 0.2 and 0.8.

7. The process of claim 1, wherein the extraction solvent is cyclohexane.

8. The process of claim 1, wherein the feed mixture is an effluent stream from a hydrocyanation process.

9. The process of claim 8, wherein the hydrocyanation process includes a 3-pentenenitrile hydrocyanation process.

10. The process of claim 9, wherein the hydrocyanation process includes a 1,3-butadiene hydrocyanation process.

11. The process of claim 1, wherein the Lewis acid is $ZnCl_2$.

* * * * *